US009318518B2

(12) United States Patent  (10) Patent No.: US 9,318,518 B2
Hermann et al.  (45) Date of Patent: Apr. 19, 2016

(54) PHOTON COUNTING DETECTOR PIXEL HAVING AN ANODE INCLUDING TWO OR MORE ALTERNATIVELY SELECTABLE AND SEPARATE SUB-ANODES

(75) Inventors: Christoph Hermann, Aachen (DE); Oliver Muelhens, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 210 days.

(21) Appl. No.: 13/979,707

(22) PCT Filed: Jan. 10, 2012

(86) PCT No.: PCT/IB2012/050105
§ 371 (c)(1),
(2), (4) Date: Jul. 15, 2013

(87) PCT Pub. No.: WO2012/098477
PCT Pub. Date: Jul. 26, 2012

(65) Prior Publication Data
US 2013/0287172 A1  Oct. 31, 2013

Related U.S. Application Data

(60) Provisional application No. 61/433,336, filed on Jan. 17, 2011.

(51) Int. Cl.
*H01L 27/146* (2006.01)
*H05G 1/56* (2006.01)
(Continued)

(52) U.S. Cl.
CPC .... *H01L 27/14609* (2013.01); *H01L 27/14603* (2013.01); *H01L 27/14643* (2013.01);
(Continued)

(58) Field of Classification Search
CPC .......... A61B 6/00; A61B 6/42; A61B 6/4208; A61B 6/4241; A61B 6/4233; A61B 6/4266; G01T 1/00; G01T 1/16; G01T 1/161; G01T 1/22; G01T 1/24; G01T 1/241; G01T 1/243; G01T 1/246; G01T 1/247; H05G 1/00; H05G 1/08; H05G 1/56; H05G 1/60; H04N 5/30; H04N 5/32; H04N 5/335; H04N 5/369; H04N 5/372; H04N 5/374; G03G 5/00; G03G 5/02; G03G 5/04; G03G 5/08; H01L 25/00; H01L 27/00; H01L 27/02; H01L 27/0203; H01L 27/04; H01L 27/10; H01L 27/1057; H01L 27/14; H01L 27/142; H01L 27/144; H01L 27/1443; H01L 27/1445; H01L 27/145; H01L 27/14601; H01L 27/14603; H01L 27/14609; H01L 27/14636; H01L 27/14643; H01L 27/14658; H01L 29/40; H01L 29/401; H01L 29/408; H01L 29/41; H01L 29/43; H01L 29/49; H01L 29/4916; H01L 29/495; H01L 29/4966; H01L 29/51; H01L 31/00; H01L 31/02; H01L 31/02016; H01L 31/0224; H01L 31/0352; H01L 31/18
USPC .............. 378/19, 91, 98, 98.8, 189, 204, 210; 250/252.1, 315.3, 370.01, 370.06, 250/370.08, 370.09, 370.12, 370.13, 250/370.14, 371, 393, 394, 395, 208.1, 250/208.2, 208.4, 214 SW, 526
See application file for complete search history.

(56) References Cited

U.S. PATENT DOCUMENTS 5,461,226 A * 10/1995 Nicoli et al. ............ 250/214 VT
6,034,373 A    3/2000 Shahar et al.
(Continued)

FOREIGN PATENT DOCUMENTS

JP  2003294845     10/2003
WO  2010073189 A1   7/2010

*Primary Examiner* — Anastasia Midkiff

(57) ABSTRACT

An imaging system (100) includes a radiation source (112) that emits radiation that traverses an examination region and a detector array (114) with a plurality of photon counting detector pixels (116) that detect radiation traversing the examination region and respectfully generate a signal indicative of the detected radiation. The photon counting detector pixel includes a direct conversion layer (122) having a first radiation receiving side (202) and second opposing side (206), a cathode (118) affixed to and covering all of or a substantial portion of the first side, an anode (120) affixed to a centrally located region (208) of the second side, wherein the anode includes at least two sub-anodes (120, 120*i*, 1202, 120N), and a metallization (124) affixed to the second side, surrounding the anode and the anode region, with a gap between the anode and the metallization. The system further includes a reconstructor (144) that reconstructs the signal to generate volumetric image data indicative of the examination region.

18 Claims, 4 Drawing Sheets

(51) Int. Cl.
  *G01T 1/24* (2006.01)
  *H04N 5/369* (2011.01)
  *A61B 6/00* (2006.01)

(52) U.S. Cl.
  CPC ............... *A61B6/4233* (2013.01); *G01T 1/24* (2013.01); *G01T 1/241* (2013.01); *G01T 1/247* (2013.01); *H01L 27/14658* (2013.01); *H04N 5/369* (2013.01); *H05G 1/56* (2013.01)

(56) References Cited

U.S. PATENT DOCUMENTS

| | | | |
|---|---|---|---|
| 6,037,595 | A | 3/2000 | Lingren |
| 7,170,049 | B2 | 1/2007 | Iwanczyk et al. |
| 2009/0080601 | A1 | 3/2009 | Tkaczyk et al. |
| 2010/0252744 | A1 | 10/2010 | Herrmann et al. |
| 2011/0155899 | A1* | 6/2011 | Dror et al. ............... 250/252.1 |

* cited by examiner

PHOTON COUNTING DETECTOR PIXEL HAVING AN ANODE INCLUDING TWO OR MORE ALTERNATIVELY SELECTABLE AND SEPARATE SUB-ANODES

FIELD OF THE INVENTION

The following generally relates to an imaging system and more particularly to an energy-resolving photon counting detector having a detector pixel with two or more alternatively selectable and separate sub-anodes and is described in connection with a computed tomography (CT) scanner. However, the following is also amenable to other imaging modalities such as x-ray and/or other imaging modalities which can employ an energy-resolving detector.

BACKGROUND OF THE INVENTION

A spectral computed tomography (CT) scanner includes a rotating portion rotatably supported by a stationary portion. The rotating portion supports an x-ray tube, which emits poly-energetic radiation (x-ray photons) that traverses an examination region and an object or subject therein, and a detector array with one or more rows of energy-resolving detectors that detect radiation traversing the examination region and generate electrical signals indicative of the detected radiation.

The electrical signals are amplified and processed by a pulse shaper to generate pulses having peak amplitudes indicative of the energy of the detected photons. A discriminator compares the amplitudes of the voltage pulses with two or more thresholds that are set in accordance with different energy levels and produces a signal, for a threshold, in response to the pulse amplitude rising above the threshold. For each threshold, a counter counts the produced signals, and an energy binner bins the counts into bins corresponding to different energy ranges. A reconstructor employs a spectral reconstruction algorithm to reconstruct the detected radiation based on the binned data.

A suitable energy-resolving photon counting detector includes a direct-conversion detector with a cadmium telluride (CdTe), cadmium zinc telluride (CdZnTe or CZT), or another direct conversion material. A direct-conversion detector generally consists of a block of semiconductor material disposed between two electrodes, a cathode and an anode, to which a voltage is applied across. Radiation illuminates the cathode side, and the x-ray photons transfer energy to electrons, which create a number of electron/hole pairs, with the electrons drifting towards anode pixels of the anode side.

Such a detector may include a metallization that surrounds each pixel anode; the metallization has been referred to as a controlling or steering electrode. Generally, the steering electrode is held at a negative electrical potential, relative to the pixel anode, but not more negative than the cathode electrical potential. This results in an electric field that guides the drifting electrons to the pixel anode. The anode, in response to receiving electrons, produces an electrical signal indicative thereof, which is conveyed to an integrated circuit (IC).

The anode for each pixel is physically and electrically bonded to a complementary bonding pad of the IC, which includes processing electronics that route the signal off the detector, for example, to the reconstructor. After bonding an IC to direct conversion material, the anode-to-IC interconnect is tested. This can be achieved by irradiating the direct conversion material and measuring the output of the detector or applying a voltage across the direct conversion material and the IC pads. In the latter case, measuring a leakage current would indicate a good interconnect whereas measuring no current would indicate a bad interconnect.

With direct-conversion photon counting detectors with detector pixel pitches (pixel center to pixel center distances) of one millimeter (1.0 mm) or less and anode diameters in a range of fifty micron (50 μm) to one hundred microns (100 μm), bonding yields of the bonds between the pixel anodes and corresponding bonding pads of the IC, using stud-bump or low temperature solder, has been less than one hundred percent (100%) such as between sixty and eighty percent (60%-80%). Detectors with such bond yields generally are either reworked or discarded, which can increase overall per detector cost, and consumes time.

One potential approach to increase the bond yield in general is to use multiple interconnects for the same detector pixel anode/bond pad pair. Unfortunately, direct-conversion photon counting detectors with steering electrodes and with detector pixel anodes having diameters in a range of fifty microns (50 μm) to one hundred microns (100 μm) are not well-suited for multiple bonds with the same detector pixel anode due to space limitations. Therefore, there is an unresolved need for other approaches for increasing the bond yield.

SUMMARY OF THE INVENTION

Aspects of the present application address the above-referenced matters and others.

According to one aspect, an imaging system includes a radiation source that emits radiation that traverses an examination region and a detector array with a plurality of photon counting detector pixels that detect radiation traversing the examination region and respectively generate a signal indicative of the detected radiation. The photon counting detector pixel includes a direct conversion layer having a first radiation receiving side and second opposing side, a cathode affixed to and covering all of or a substantial portion of the first side, an anode affixed to a centrally located region of the second side, wherein the anode includes at least two sub-anodes, and a metallization affixed to the second side, surrounding the anode, with a gap between anode and metallization. The system further includes a reconstructor that reconstructs the signal to generate volumetric image data indicative of the examination region.

According to another aspect, a method includes detecting radiation traversing an examination region with a photon counting detector pixel, wherein the photon counting detector pixel includes an anode having at least two physically and electrically separate sub-anodes collectively surrounded by a metallization, wherein the at least two sub-anodes are coupled to corresponding sub-bond pads of a substrate, and an electrical switch electrically connects only a single one of the at least two sub-bond pads with processing electronics of the substrate.

According to another aspect, a detector array includes processing electronics and at least one photon counting detector pixel, including an anode having at least two separate sub-anodes collectively surrounded by a steering electrode, wherein only a single one of the at least two sub-anodes is in electrical communication with the processing electronics.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
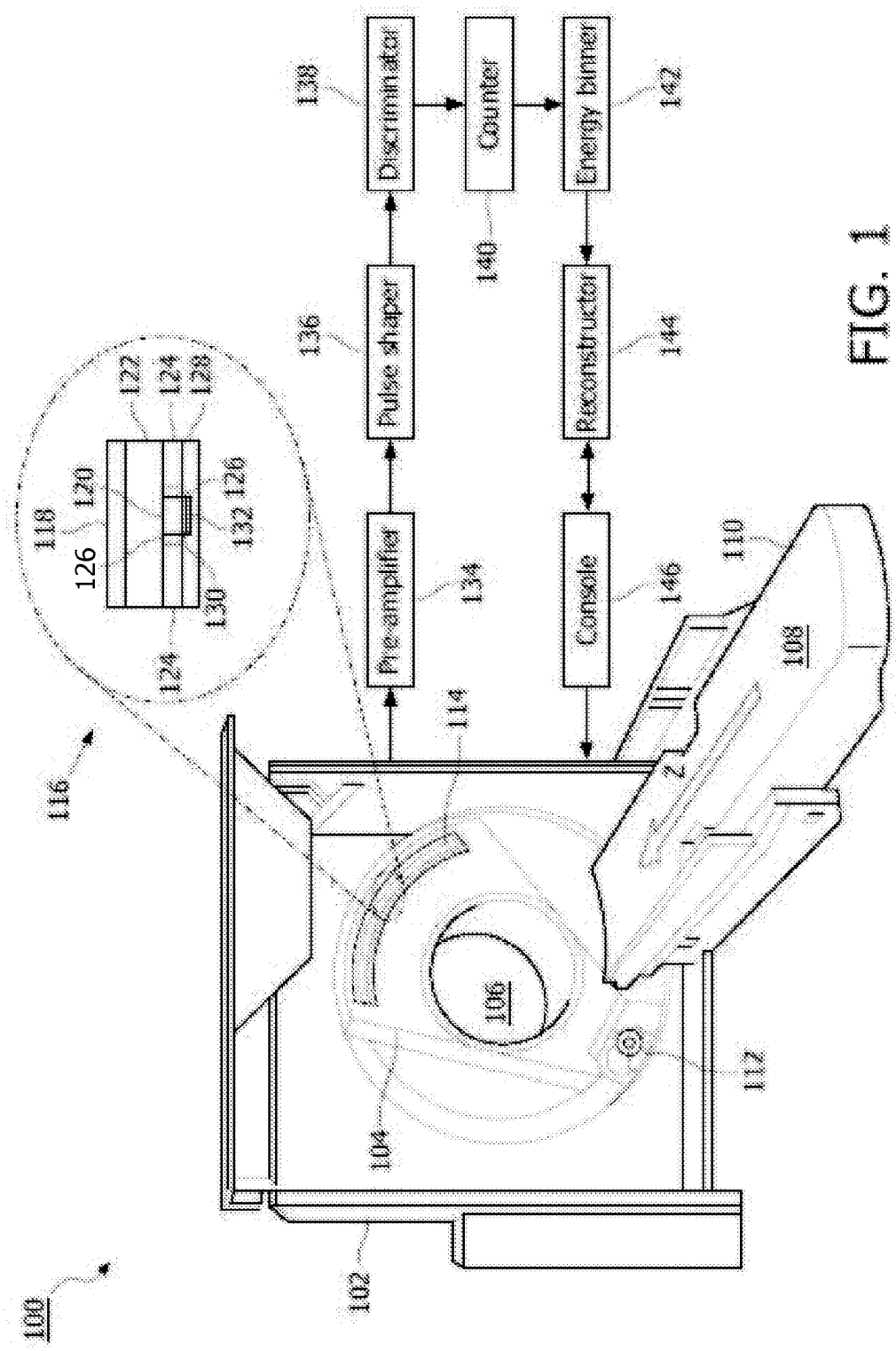
FIG. 1 schematically illustrates an imaging system including a photon counting detector pixel having at least two sub-anodes in which only a single one of the sub-anodes is utilized.

FIG. 1 schematically illustrates an imaging system such as a computed tomography (CT) scanner 100. The scanner 100 includes a stationary gantry 102 and a rotating gantry 104, which is rotatably supported by the stationary gantry 102. The rotating gantry 104 rotates around an examination region 106 about a longitudinal or z-axis 108 one or more times for one or more data acquisition cycles. A patient support 110, such as a couch, supports an object or subject, such as an animal or human patient, in the examination region 106.

A radiation source 112, such as an x-ray tube, is supported by and rotates with the rotating gantry 104 around the examination region 106. The radiation source 112 emits poly-energetic radiation (x-ray photons) that is collimated by a source collimator to produce a generally fan, wedge, or cone shaped radiation beam that traverses the examination region 106. A radiation sensitive detector array 114 includes a one or two dimensional array of detector pixels that respectively detect radiation that traverses the examination region 106 and generate electrical signals (e.g., a current or a voltage) indicative of the detected radiation.

The illustrated detector array 114 includes an energy-resolving photon counting detector array, a cross section of a portion of which for a single detector pixel is shown at 116 and includes a cathode 118, an anode 120, and a direct-conversion material or layer 122 (e.g., cadmium telluride (CdTe), cadmium zinc telluride (CdZnTe or CZT), etc. disposed there between. A metallization or steering electrode 124 is affixed to the direct-conversion material or layer 122 surrounding the anode 120 and separated therefrom by a gap 126. A substrate 128 includes electronics 132, such as an integrated circuit (IC), an application specific integrated circuit (ASIC) or the like, and a bond pad 130 for electrically coupling the anode 120 and the electronics 132.

As described in greater detail below, the anode 120 includes a plurality of sets of sub-anodes, each set corresponding to a different detector pixel and including more than two physically and electrically separate sub-anodes collectively surrounded by the steering electrode metallization 124, and the substrate 128 includes a plurality of complementary sets of sub-bonding pads, each set corresponding to a different detector pixel and including sub-bonding pads complementary to the sub-anodes for that pixel. Complementary sub-anode/sub-pad pairs are physically and electrically coupled via bump-bonding, lower temperature solder, and/or other bonding approaches, and the electronics 132 is configured to selectively electrically connect and disconnect the sub-bond pads with processing and/or readout electronics of the substrate 128, and only connects a single one of the sub-bond pads of a detector pixel, at any given time, with the electronics.

In one instance, including multiple sub-anodes in each set of anodes for each detector pixel and multiple corresponding sub-bonding pads in the substrate 128 provides redundant sub-anode/pad pairs for each detector pixels. As such, if, after bonding the sub-anodes to the sub-bond pads, one or more, but not all of these interconnects, turn out to be unusable (e.g., lack a suitable electrical connection), the substrate 128 can be configured to select a sub-anode/pad pair with a usable interconnect (e.g., one having a suitable electrical connection). This may facilitate improving the bond yield for a detector pixel, for example, up to one hundred percent (100%), such as ninety percent (90%) or higher, relative to a configuration in which the detector array 114 includes direct conversion detectors with only a single anode (i.e., no sub-anodes) for each detector pixel.

An optional pre-amplifier 134 amplifies each electrical signal output from the detector array 114.

A pulse shaper 136 processes the amplified electrical signal for a detected photon and generates a corresponding analog signal that includes a pulse such as a voltage or other pulse indicative of a detected photon. In this example, the pulse has peak amplitude that is indicative of the energy of the detected photon.

An energy-discriminator 138 energy-discriminates the pulses. In this example, the energy discriminator 138 includes a plurality of comparators that respectively compare the amplitude of the pulses with a threshold that corresponds to a particular energy level. Each comparator produces an output such as high or low signal that is indicative of whether the amplitude of the pulse exceeds its threshold.

A counter 140 counts the output signals respectively for each threshold. The counter 140 may include a single counter or individual sub-counters for each threshold.

An energy-binner 142 energy-bins the counts into energy ranges or bins corresponding to ranges between the energy thresholds. The binned data is used to energy-resolve the detected photons.

A reconstructor 144 selectively reconstructs the detected radiation based on the spectral characteristics of the detected photons. For example, the binned data can be used to generally isolate different types of organic materials having different photon absorbing characteristics such as bone, organic tissue, fat and/or the like, locate contrast enhancement materials, and/or otherwise process the detected signals based on spectral characteristics.

A general purpose computing system serves as an operator console 146, and includes an output device such as a display and an input device such as a keyboard, mouse, and/or the like. Software resident on the console 146 allows the operator to control the operation of the system 100, for example, allowing the operator to select a spectral imaging protocol, initiate scanning, etc.

Figure 2:
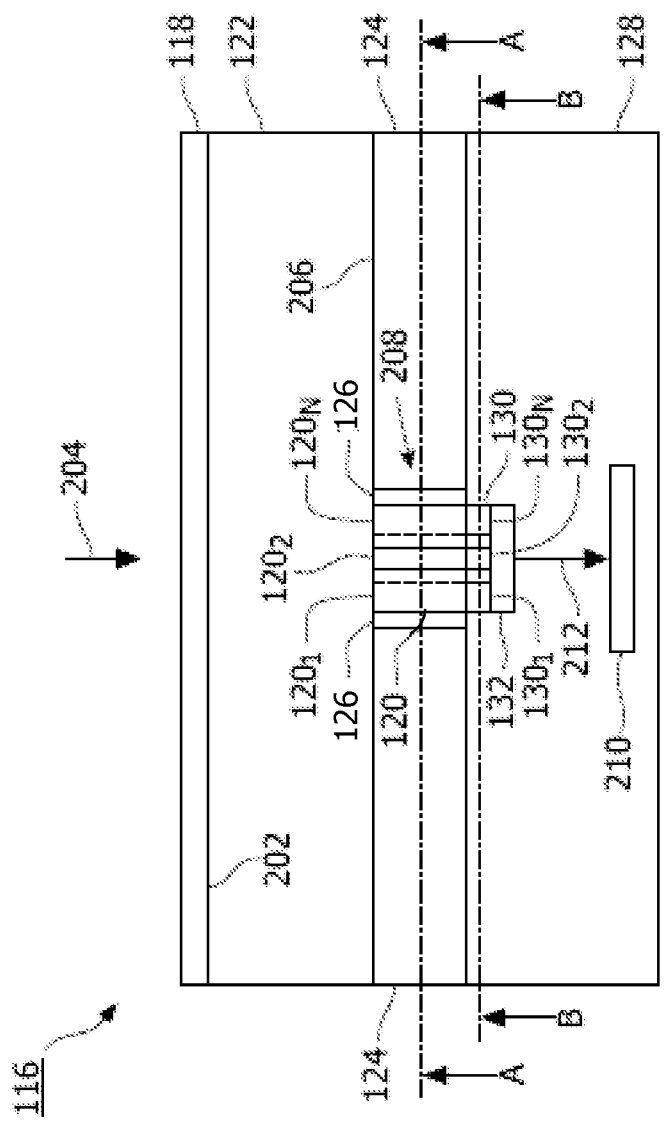
FIG. 2 schematically illustrates a cross-sectional side view of an example of the photon counting detector pixel.

FIG. 2 schematically illustrates the sub-portion 116. Note that the detector array 114 includes a one or two dimensional array of such portions 116.

The cathode 118 is arranged on a first radiation receiving side 202 of the direct conversion material or layer 122 that faces the direction of incoming radiation 204 and extends over the entire or substantially the entire side 202. A cathode voltage source (not shown) is applied to the cathode 118 and biases the cathode 118 at a negative voltage potential relative to the anode 120.

The anode 120 includes sub-anodes $120_1, 120_2, \ldots, 120_N$, where N is an integer equal to or greater than two (2), is arranged on a second opposing side 206 of the direct conversion material or layer 122. In the illustrated embodiment, the anode 120 is about centered or centrally located with respect to an anode region 208 of the detector pixel 116. An anode voltage source is applied to the anode 120 and biases the anode at a voltage potential more positive than the voltage potential of the cathode 118.

The steering electrode 124 is arranged on the second side 206 of the direct conversion material or layer 122, as a conductive layer surrounding the anode 120, covering a sub-portion of the side 206 outside of the area covered by the anode 120 and separated from the sub-anodes at least by the gap 126. A steering electrode voltage source (not shown) biases the steering electrode 124 at positive voltage potential relative to the cathode 118 and a negative voltage potential relative to the anode 120.

Figure 3:
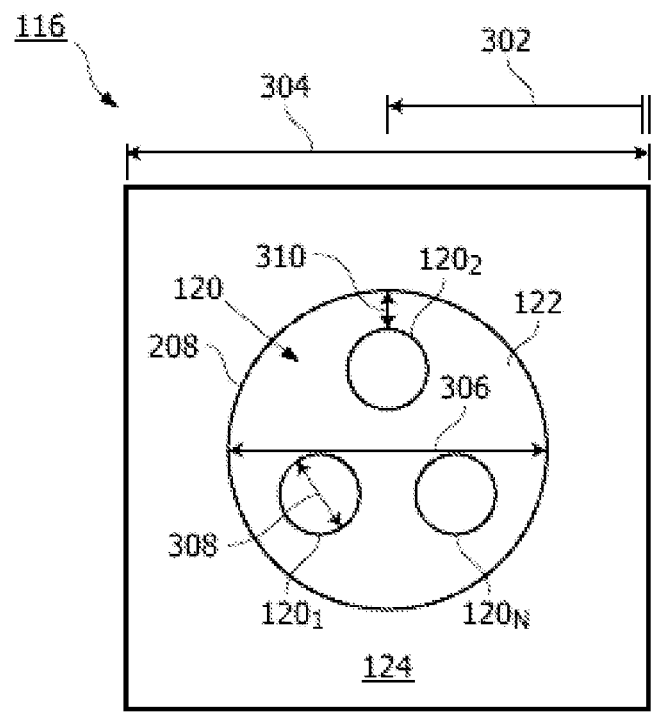
FIG. 3 schematically illustrates a cross-sectional view of the photon counting detector pixel along A-A of FIG. 2 showing sub-anodes.

FIG. 3 schematically illustrates a cross sectional view of the detector pixel 116 along line A-A of FIG. 2, showing an example arrangement of the anode 120 in connection with the steering electrode 124. In FIG. 3, three sub-anodes are shown for explanatory purposes. However, it is to be appreciated that in other embodiment N is equal to two or more than three.

In the illustrated embodiment, a pitch 302 represents a detector pixel center to detector pixel center distance and is in a range of about two hundred microns (200 μm) to about one and a half millimeters (1.5 mm), for example, from about three hundred microns (300 μm) to about one millimeter (1.0 mm). Generally, a length 304 of a detector pixel is equal to the pitch or is a little larger than the pitch 302 due to any spacing between pixels. The illustrated pixel 116 is square. However, it is to be appreciated the suitable pixel shapes also rectangular, elliptical, circular, hexagonal, and/or other shape.

A diameter 306 of the anode region 208 is in a range of about one hundred microns (100 μm) to about three hundred microns (300 μm), for example, at about two hundred microns (200 μm). A diameter 308 of a sub-anode $120_1, 120_2, \ldots, 120_N$ is in a range of about twenty-five microns (25 μm) to about one hundred and fifty microns (150 μm), for example, from about fifty microns (50 μm) to about hundred microns (100 μm).

A shortest distance 310 of the gap 126 between the sub-anodes $120_1, 120_2, \ldots, 120_N$ and the steering electrode 124 is in a range of about ten microns (10 μm) to about forty microns (40 μm), for example, from about twenty microns (20 μm) to about thirty microns (30 μm). Generally, the distance 310 may correspond to distance at which a predetermined leakage current is not exceeded. A passivation material may be disposed between the sub-anodes $120_1, 120_2, \ldots, 120_N$ and the steering electrode 124.

In the illustrated embodiment, the sub-anodes $120_1, 120_2, \ldots, 120_N$ and the anode region 208 are circular in shape. Such a shape is well-suited for optimizing the steering affects of the electrical field produced by the steering electrode 124, relative to a shape that has corners. However, other shapes such as elliptical, hexagonal, rectangular, squared, and/or other shapes are contemplated herein.

Returning to FIG. 2, the bond pad 130 is located below at least a sub-portion the anode 120 and includes sub-pads anodes $130_1, 130_2, \ldots, 130_N$, one corresponding to each of the sub-anodes $120_1, 120_2, \ldots, 120_N$. The switching electronics 132 electrically couples the bond pads 130, via a pathway 212, to other electronics 210 carried by the substrate 128. As discussed herein, the switching electronics 132 are configured to selectively electrically couple only one of the sub-pads $130_1, 130_2, \ldots, 130_N$ to the other electronics 210, at any given time.

After bonding the substrate 128 to the steering electrode 124 affixed to the direct conversion material or layer 122, test irradiation or a voltage can be applied to each detector pixel to determine which sub-pad 130 to electrical couple to the other electronics 210. For this, each switch of the electronics 132 is individually closed so that only one of the sub-pads 130 is connected to the other electronics 210, and then the detector pixel 116 is tested for that sub-pad 130. Sub-pads $130_1, 130_2, \ldots, 130_N$ not connected to the readout electronics 210 are kept at a floating voltage potential.

Figure 4:
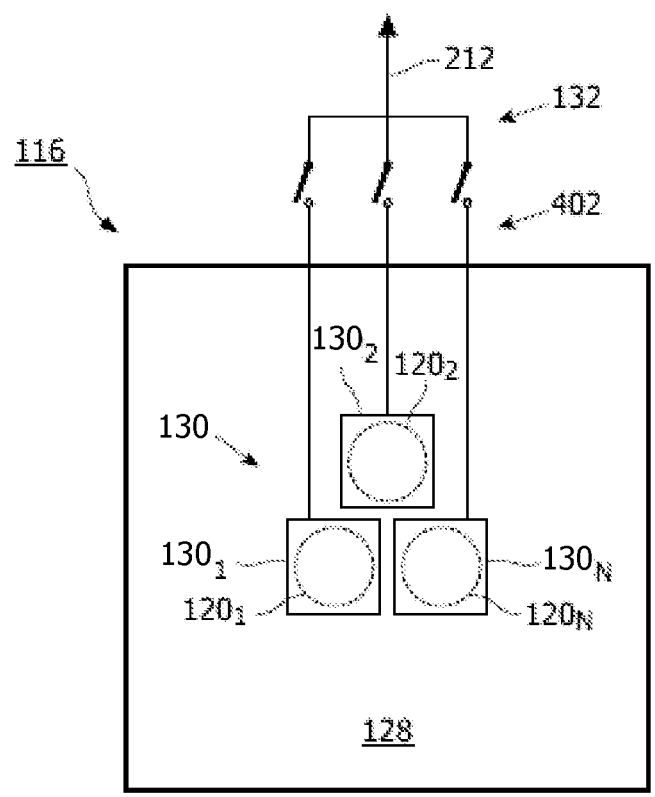
FIG. 4 schematically illustrates a cross-sectional view of the photon counting detector pixel along B-B of FIG. 2 showing sub-bond pads.

FIG. 4 schematically illustrates a cross sectional view of the detector pixel 116 along line B-B of FIG. 2, showing an example arrangement of the bond pad 130 in connection with the anode 120 and the steering electrode 122.

As shown, the sub-pads anodes $130_1, 130_2, \ldots, 130_N$ are aligned with and physically and electrically coupled to the sub-anodes $120_1, 120_2, \ldots, 120_N$. Separate pathways 402 respectively electrically couple the sub-pads $130_1, 130_2, \ldots, 130_N$, with corresponding respective individual switches of the switching electronics 132, which individually electrically connect and disconnect the sub-pads $130_1, 130_2, \ldots, 130_N$ to the processing electronics 210.

Figure 5:
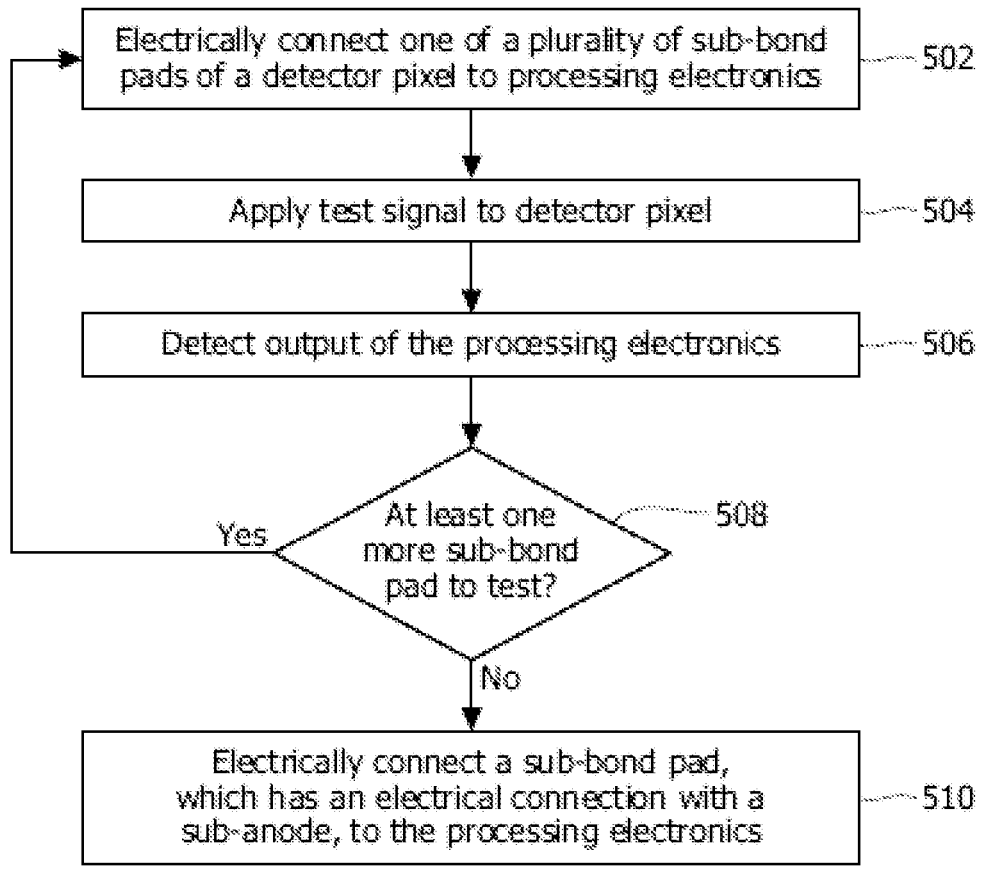
FIG. 5 illustrates a method for selecting a sub-anode/sub-bond pad pair of a detector pixel.

FIG. 5 illustrates an example method for selecting only a single sub-anode of a plurality of available sub-anodes of a counting detector pixel and electrically connecting only the single sub-anode to processing electronics of the counting detector pixel.

It is to be appreciated that the ordering of the acts in the methods described herein is not limiting. As such, other orderings are contemplated herein. In addition, one or more acts may be omitted and/or one or more additional acts may be included.

At 502, the switching electronics 132 are configured so that only one of a plurality of the sub-bond pads $130_1, 130_2, \ldots, 130_N$ is in electrical communication with the processing electronics 210.

At 504, a test signal (e.g., radiation, a voltage, etc.) is applied to the photon counting detector pixel 116.

At 506, the output of the processing electronics 210 is detected. Generally, the processing electronics 210 for the detector pixel 116 generates an output signal in response to an electrical connection between sub-bond pad $130_1, 130_2, \ldots, 130_N$ and the sub-anode $120_1, 120_2, \ldots, 120_N$ bonded to sub-bond pad $130_1, 130_2, \ldots, 130_N$.

At 508, acts 502-506 are repeated for the other sub-bond pads $130_1, 130_2, \ldots, 130_N$.

At 510, the switching electronics 132 are configured so the single sub-bond pad $130_1, 130_2, \ldots, 130_N$ in electrical communication with the processing electronics 210 is a sub-bond pad $130_1, 130_2, \ldots, 130_N$ in electrical communication with a corresponding sub-anode $120_1, 120_2, \ldots, 120_N$.

Figure 6:
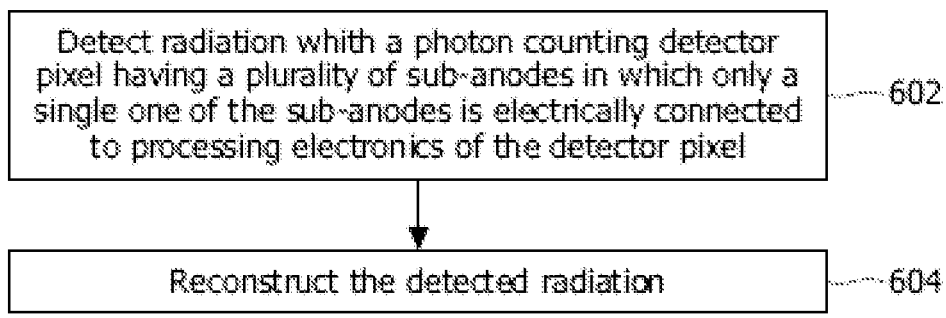
FIG. 6 illustrates a method for detecting radiation in connection with an imaging system.

FIG. 6 illustrates an example method for employing a counting detector pixel in which only a single sub-anode of a plurality of available sub-anodes of the counting detector pixel is electrically connected to processing electronics of the counting detector pixel.

It is to be appreciated that the ordering of the acts in the methods described herein is not limiting. As such, other orderings are contemplated herein. In addition, one or more acts may be omitted and/or one or more additional acts may be included.

At 602, radiation traversing an examination region is detected with a photon counting detector pixel having an anode with at least two separate sub-anodes collectively surrounded by a metallization, wherein the at least two separate sub-anodes are respectively physically and electrically coupled to corresponding sub-bond pads of an integrated circuit, and only a single one of the at least two sub-bond pads is in electrical communication with the integrated circuit.

At 604, the detected radiation is reconstructed to generate volumetric image data.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. An imaging system, comprising:
   a radiation source that emits x-ray radiation that traverses an examination region;
   a detector array with a plurality of photon counting detector pixels that detect x-ray radiation traversing the examination region and respectively generate a signal indicative of the detected x-ray radiation, a photon counting detector pixel, comprising:
      a direct conversion layer having a first radiation receiving side and second opposing side;
      a cathode affixed to and covering all of or a substantial portion of the first side;
      an anode affixed to a centrally located region of the second side, wherein the anode includes at least two sub-anodes; and
      a metallization affixed to the second side, surrounding the anode with a gap between the anode and the metallization;
   a substrate having at least two bonding pads, one for each of the at least two sub-anodes, wherein each of the at least two bonding pads is physically and electrically coupled to a different one of the at least two sub-anodes;
   processing electronics;
   switching electronics configured to alternatively electrically couple only a single one of the at least two bonding pads to the processing electronics; and
   a reconstructor that reconstructs the signal to generate volumetric image data indicative of the examination region.

2. The imaging system of claim 1, wherein the sub-anode physically and electrically coupled to the bonding pad is maintained at a predetermined anode electrical potential.

3. The imaging system of claim 2, wherein the other sub-anodes are kept at a floating electrical potential.

4. The imaging system of claim 1, wherein the gap includes a passivation material.

5. The imaging system of claim 1, wherein the centrally located region is about one hundred to three hundred microns in diameter.

6. The imaging system of claim 1, wherein a sub-anode is about twenty-five to one hundred and twenty-five microns in diameter.

7. The imaging system of claim 1, wherein the gap between anode and metallization is at least in a range from about ten microns to about forty microns.

8. The imaging system of claim 1, wherein a center to center distance between detector pixels is in a range of about two hundred microns to about one and a half millimeters.

9. The imaging system of claim 1, wherein a detector pixel length is in a range of about two hundred microns to about one and a half millimeters.

10. The imaging system of claim 1, wherein the at least two sub-anodes is three sub-anodes.

11. The imaging system of claim 1, wherein a bond yield corresponding to having an electrical connection between at least one sub-pad and at least one corresponding bond pad is in a range of about ninety to one hundred percent.

12. The imaging system of claim 1, wherein the direct conversion layer includes a direct conversion layer including at least one of cadmium telluride or cadmium zinc telluride.

13. A method, comprising:
   detecting x-ray radiation traversing an examination region with a photon counting detector pixel, wherein the photon counting detector pixel includes an anode having at least two physically and electrically separate sub-anodes collectively surrounded by a metallization, wherein the at least two sub-anodes are coupled to corresponding sub-bond pads of a substrate, and an electrical switch electrically connects only a single one of the at least two sub-bond pads with processing electronics of the substrate.

14. The method of claim 13, further comprising:
   maintaining the sub-anode coupled to the single one of the at least two bond pads at a predetermined anode electrical potential.

15. The method of claim 13, further comprising:
   maintaining the sub-anode coupled to a bond pad not electrically connected to the processing electronics at a floating electrical potential.

16. The method of claim 13, further comprising:
   determining an interconnect between a sub-anode and a corresponding sub-bond pad provides an electrical pathway between the sub-anode and the sub-bond pad and, in response, selecting the corresponding sub-bond pad as the single one of the at least two sub-bond pads in electrical communication with the processing electronics.

17. The method of claim 13, further comprising:
   determining a bond between a sub-anode and a corresponding sub-bond pad does not provide an electrical pathway between the sub-anode and the sub-bond pad and, in response, disconnecting the sub-bond pad from the processing electronics.

18. An X-ray detector array, comprising:
   processing electronics; and
      at least one photon counting detector pixel, including an anode having at least two separate sub-anodes collectively surrounded by a steering electrode, wherein only a single one of the at least two sub-anodes is in electrical communication with the processing electronics.

* * * * *